(12) United States Patent
Worthington

(10) Patent No.: US 6,938,354 B2
(45) Date of Patent: Sep. 6, 2005

(54) MEASUREMENT MARKING, SCRIBING AND SCORING DEVICE

(75) Inventor: Gary Landon Worthington, Thousand Oaks, CA (US)

(73) Assignee: Cole Scientific, Inc., Moorpark, CA (US)

(*) Notice: Subject to any disclaimer, the term of this patent is extended or adjusted under 35 U.S.C. 154(b) by 0 days.

(21) Appl. No.: 10/322,397

(22) Filed: Dec. 17, 2002

(65) Prior Publication Data

US 2003/0154615 A1 Aug. 21, 2003

Related U.S. Application Data

(60) Provisional application No. 60/358,824, filed on Feb. 21, 2002.

(51) Int. Cl.$^7$ ................................................. G01B 3/10
(52) U.S. Cl. .............................. 33/668; 33/768; 33/770
(58) Field of Search .......................... 33/755, 757, 758, 33/759, 768, 770, 668

(56) References Cited

U.S. PATENT DOCUMENTS

| | | | |
|---|---|---|---|
| 812,322 A | * | 2/1906 | Badger ........................ 33/668 |
| 3,262,211 A | * | 7/1966 | Beckett ....................... 33/668 |
| 3,336,678 A | * | 8/1967 | Chamberlain et al. ........ 33/668 |
| 3,526,964 A | * | 9/1970 | Clark, Jr. ..................... 33/761 |
| 3,802,083 A | * | 4/1974 | Freed .......................... 33/668 |
| 4,667,412 A | * | 5/1987 | Carlson ........................ 33/770 |
| 4,934,054 A | * | 6/1990 | Morozumi .................. 33/27.12 |
| 4,965,941 A | * | 10/1990 | Agostinacci ................. 33/668 |
| 5,134,784 A | * | 8/1992 | Atienza ....................... 33/668 |
| 5,295,308 A | * | 3/1994 | Stevens et al. ............... 33/770 |
| 5,671,543 A | * | 9/1997 | Sears .......................... 33/668 |
| 5,829,152 A | * | 11/1998 | Potter et al. .................. 33/668 |
| 6,032,379 A | * | 3/2000 | Usami ........................ 33/758 |
| 6,041,513 A | * | 3/2000 | Doak .......................... 33/668 |
| 6,497,050 B1 | * | 12/2002 | Ricalde ....................... 33/770 |
| 6,574,881 B2 | * | 6/2003 | Cole, III ...................... 33/668 |
| 6,637,125 B2 | * | 10/2003 | Scarborough ................ 33/768 |

* cited by examiner

Primary Examiner—Christopher W. Fulton
Assistant Examiner—Madeline Gonzalez
(74) Attorney, Agent, or Firm—Aaron T. Borrowman; Kelly Lowry & Kelley, LLP

(57) ABSTRACT

A measurement marking and scoring device includes a platform configured to be affixed to a base of a tape measure. A marking member extends from the platform and defines a sharpened edge or point marking surface at a lower end thereof. An alignment tab extends from the marking member so as to be positioned over indicia of a tape extended from the tape measure so that measurement marks or score lines can be created on a working surface upon application of pressure to the marking member or tape measure. In another form, the device is integrally formed into a tape measure such that the marking member extends from a front edge of the tape measure.

14 Claims, 3 Drawing Sheets

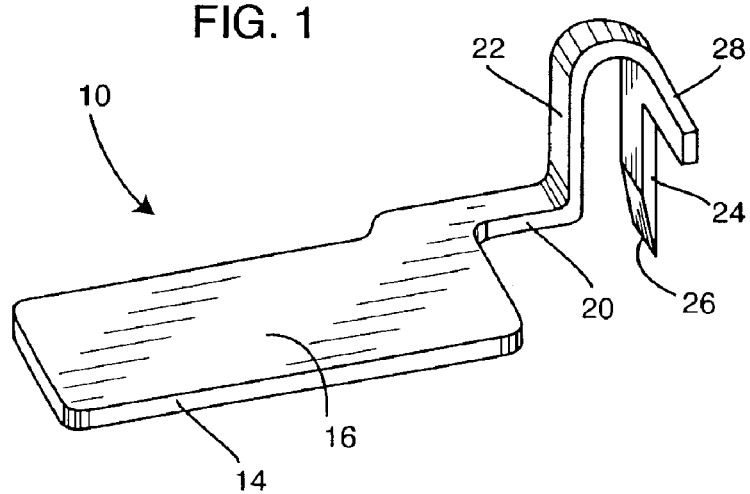
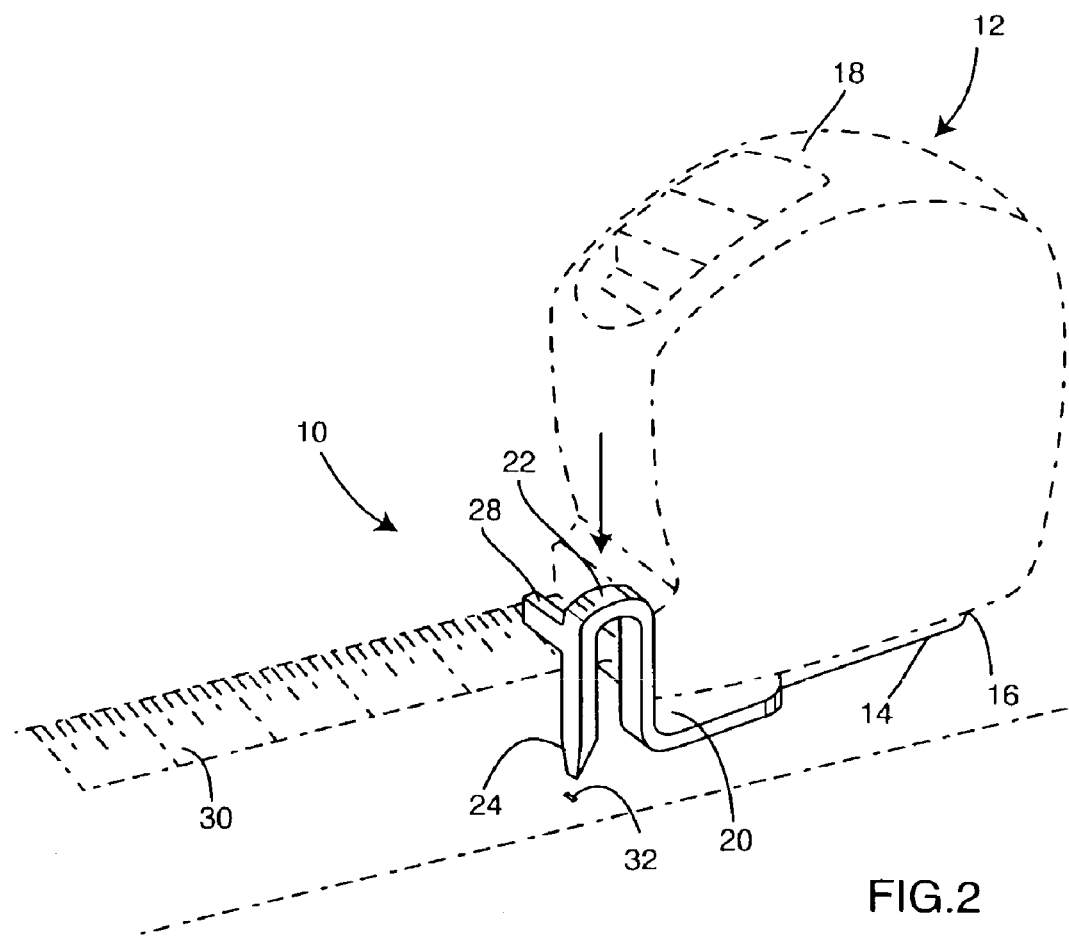

//MEASUREMENT MARKING, SCRIBING AND SCORING DEVICE

RELATED APPLICATION

This application claims priority from U.S. Provisional Application Ser. No. 60/358,824, filed Feb. 21, 2002.

BACKGROUND OF THE INVENTION

The present invention generally relates to measuring devices. More particularly, the present invention relates to a measurement marking and scoring device in the form of an attachment to a tape measure, or as an integral extension of a tape measure.

Conventional retractable tape measures, commonly used in the carpentry and construction industries as well as for general home repairs, include a tape with measurement markings and a housing for storing the tape. The far end of the tape is attached to a retraction mechanism inside the housing, whereby the tape can be automatically retracted inside the housing for storage. Typically, such tape measures include a locking mechanism so the tape can be locked in various extended positions when in use. Also, conventional tape measures include an attachment at the free end of the tape, in the form of a downwardly depending tab, also called a "hook", that can be engaged with the edge of a work surface.

Often it is desirable to mark, scribe and/or scroll a line at a measured distance parallel to an edge of a work piece such as wood, drywall, plexiglass, acoustic ceiling tiles, pipe and a host of other building materials. This involves several steps. Typically, the housing of the tape measure is aligned with an edge of the work piece with one hand, the downwardly depending tab or "hook" of the tape measure hooked onto an edge of the work piece, or held by the other hand. A marking instrument, such as a pencil, is typically used to create a marking point or line transverse to the axis of the extended tape at the proper measurement marking on the tape. It is cumbersome to hold the pencil or marker firmly in position at the end of the tape with conventional tape measures. Also, pencil points are easily and quickly rounded and dulled, resulting in marks or scribed lines that are less than precise at the measured point.

Moreover, the feat of holding the tape measure housing, properly maintaining sufficient tension in the extended tape to keep the downwardly depending tab locked against the edge of the work surface, retrieve a marker or pencil in the free hand, and properly align and mark is cumbersome and difficult. Sometimes, this process results in inaccurate markings.

After a measured point is drawn and/or a line scribed on the work piece material, there is typically a requirement to cut the work material at that line. This requires an additional subsequent step of cutting or scribing the work material with a saw or blade of some sort. When the work material is drywall, which is one of the most common work materials used in carpentry and construction work, it would be of great value if there were a measurement marking device that in addition to having the capability of scribing the material could also score the material sufficiently to replace the separate step of scoring the drywall with a knife blade to allow it to be broken at the score line.

Accordingly, there is a need for a measurement marking, scribing and scoring device which is attachable to a tape measure or can be incorporated directly into the design of the tape measure housing in order to free both hands for use in operating the tape measure and attain an accurate marking, while also providing the capability of scribing and scoring the work material. The present invention fulfills these needs, and provides other related advantages.

SUMMARY OF THE INVENTION

The present invention resides in a measurement and marking and scoring device which enables both hands to be free to operate the tape measure, while attaining an accurate measurement marking or line score. The measurement marking scoring device generally comprises a marking member extending beyond a front edge of a tape measure and having a marking surface directed downwardly and configured to create a mark or score line on a working surface, corresponding to a measurement marking, upon application of pressure to the marking member or tape measure.

In one embodiment, the device includes a platform configured to be affixed to the base of the tape measure. A marking member extends from the platform so as to be positioned beyond a front edge of an attached tape measure. A marking surface is formed on a downwardly directed, lower end of the marking member. The marking surface comprises a sharpened edge or point so as to create a measurement mark or score line on a working surface upon application of pressure to the marking member or tape measure. In a particularly preferred embodiment, the marking member comprises a neck extending from the platform to an inverted U-shaped head positioned beyond the front edge of the tape measure, and which defines the marking surface at a lower end thereof. An alignment tab extends from the marking member so as to be positioned over indicia of a tape extended from the tape measure to properly align and create the mark or score line.

In another embodiment, the measurement marking and scoring device is formed integrally with a tape measure such that the marking member extends beyond the front edge of the tape measure. Typically, the marking member comprises a generally inverted L-shaped metallic extension extending from the tape measure and defining a marking surface at a lower end thereof. The marking surface comprises a sharpened edge or point of the end of the extension, configured to create a measurement mark or score line on a working surface upon application of pressure to the marking member or tape measure. An alignment tab extends from the marking member so as to be positioned over indicia of a tape extending from the tape measure to aid in creating an accurate measurement mark or score line.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 1 is a perspective view of a measurement marking device embodying the present invention;

FIG. 2 is a perspective view of the measurement marking device of FIG.1 attached to a tape measure, illustrated in phantom, and creating a measurement marking;

DETAILED DESCRIPTION OF THE PREFERRED EMBODIMENTS

Figure 3:
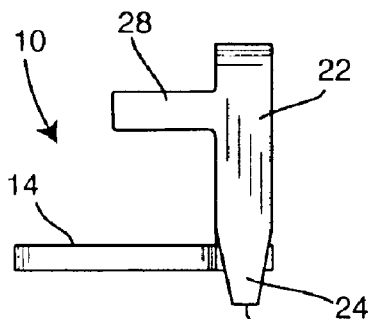
FIG. 3 is a front elevational view of the measurement marking device of the present invention.
Figure 4:
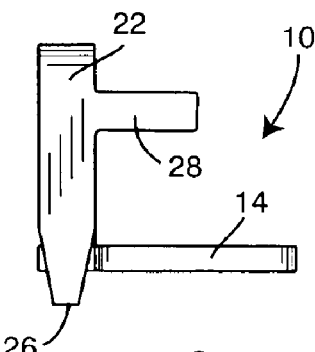
FIG. 4 is a rear elevational view of the measurement marking device of the present invention.
Figure 5:
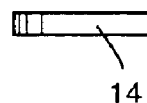
FIG. 5 is a side elevational view of the measurement marking device of the present invention.
Figure 6:
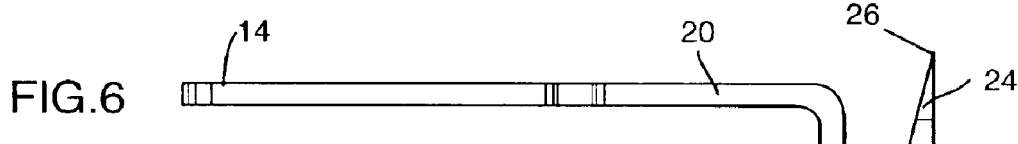
FIG. 6 is a side elevational view taken from the opposite side of FIG. 5.
Figure 7:
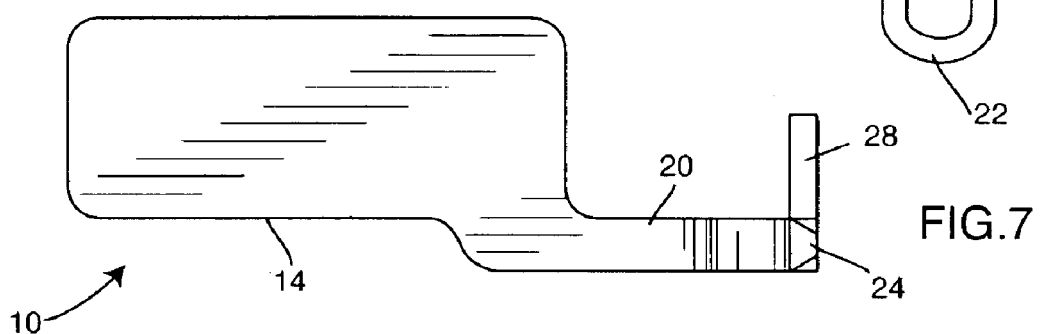
FIG. 7 is a top planar view of the measurement marking device of the present invention.
Figure 8:
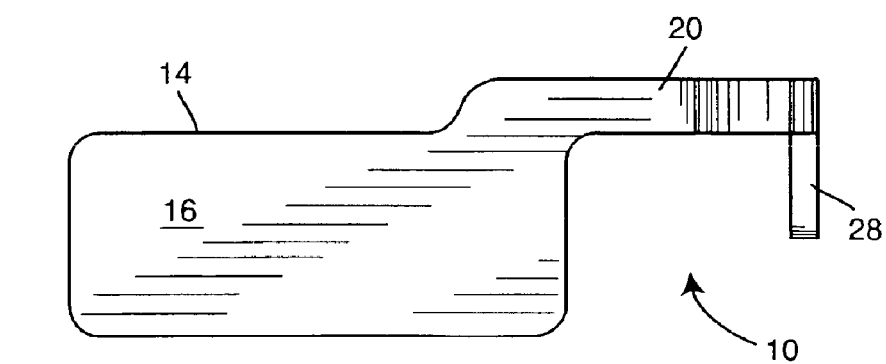
FIG. 8 is a bottom planar view of the measurement marking device of the present invention.
Figure 9:
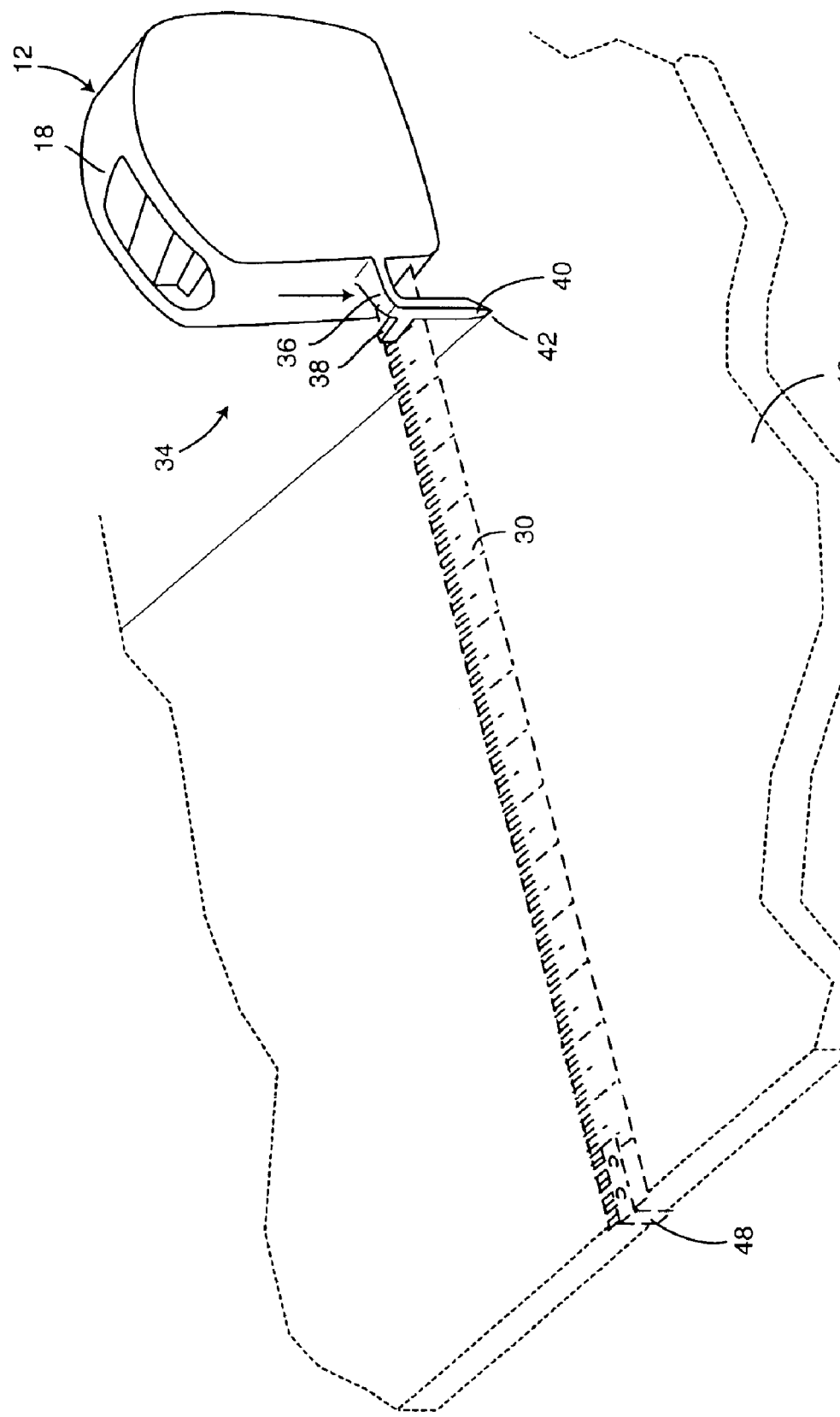
FIG. 9 is a perspective view of a tape measure having a marking member integrally formed therewith, and forming a scribe line on a sheet of working material, illustrated in phantom.

As shown in the drawings for purpose of illustration, the present invention is concerned with a measurement marking device, generally referred to by the reference number 10 in FIGS. 1–8 and by the reference number 34 in FIG. 9. The device 10 or 34 is designed and configured to assist in measurement markings creating, scoring lines, and the like without the need of external marking tools, such as pencils or pens.

With reference to FIGS. 1–8, in a first embodiment, the device 10 includes a generally planar body section having a generally top surface 16 defining a seat or platform to which bottom surface of a tape measure housing 18 is attached, such as by adhesive, double sided tape, or other appropriate means known in the art. The body 14 is typically rectangular in shape, although not limited to such configuration, and sized such so as to accommodate a tape measure 12. The overall size and dimensions of the device can vary depending upon the size of the intended tape measure 12 to be used with the device 10, or designed as a one-size-fits all size which would allow the attachment and placement of smaller tape measures 12 on the platform 16.

A marking member extends from the body 14 so as to be generally positioned in front of a leading edge of the tape measure housing 18. The marking member includes a neck 20 that extends from a front corner of the body 14 that is typically the same thickness and generally planar with the body 14. An inverted U-shaped head 22 extends from the neck 20 in generally serpentine fashion to a nose 24 having a marking surface in the form of a sharpened edge, point or tip 26 that is generally even with, or extends slightly below, the lower surface of the body 14. An alignment tab 28 extends from the head 22 above the nose 24 so as to be in alignment with the marking surface 26 and be positioned over measurement indicia of a tape 30 extended from the housing 18 of the tape measure 12. Typically, the alignment tab 28 extends generally transverse to the head 22 and nose 24 so as to extend over the tape 30.

The device 10 configured as an attachment to a pre-existing tape measure 12 is particularly useful as the device 10 can be offered rather inexpensively. As mentioned above, the device 10 can be sized and configured so as to be attached to a variety of tape measures 12 of differing sizes. Thus, a construction worker or home owner can attach the device 10 to a tape measure 12 which he or she already owns.

With reference now to FIG. 9, a measurement marking and scoring device 34 is illustrated wherein the tape measure 12 has integrally built therein the ability to form the measurement markings and score lines described above. The marking member 36 is in the form of a generally inverted L-shaped extension, which extends from a leading surface or edge of the tape measure housing 18. A lower end 40 of the marking member 36 defines a marking surface 42 in the form of a sharpened edge, tip, point, etc. An alignment tab 38 extends from the marking member 36 above the marking surface 42, and in alignment therewith, so that it can be positioned over indicia on the extended tape 30 in order to facilitate alignment of the proper marking indicia 30 with the marking surface 42 to obtain an accurate measurement marking.

With particular reference now to FIG. 2, in use, the tape measure 12 is attached to the platform 16 of the device 10 such that the tape 30 thereof extends from the housing 18 towards and past the head 22, nose 24 and alignment tab 28. Alternatively, the tape measure marking device 34 is used. The user of the device 10 engages the downwardly depending tab of the tape measure on an edge of the work surface (not shown), or holds the extended end with one hand, moves the device 10 and attached tape measure 12 to the desired length with the other hand, looks downwardly upon alignment tab 28 to ensure that the intended marking indicia on the tape 30 is in alignment with the tab 28, and presses downwardly on the head 22 or housing 18 so that the sharpened tip or edge of nose 24 forms a measurement marking 32 on the working surface.

Due to the fact that the sharpened tip or edge 26 of the nose 24 typically forms a straight line marking, the user can more easily square the resulting marking line intended to be cut, etc., much more easily than marking by hand which marking oftentimes is slightly slanted or skewed. Of course, the sharpened end 26 can also be in the form of a point or any other suitable configuration to form the appropriate marking. In a particularly preferred embodiment, the marking surface 26 or 42 is formed by creating a dual-beveled edge at the nose 24 or end 40 of the marking member. This creates a generally sharpened edge or tip which due to the bevels formed on the end 40 of the marking member 36 maintains its ability to form marks 32 and score lines 44. As will be appreciated by those skilled in the art, a series of markings 32 can be made by continuing to extend the device 10 and tape measure 12 and pressing downwardly upon head 22 at the appropriate tape measurement markings as described above. If the working surface does not lend itself to having a depression formed by sharpened edge 26, the device 10 and tape measure 12 can be moved up and down transverse to the axis of the tape 30 in order to scratch a marking on the metal or other hard surface.

With reference to FIG. 9, marking surface 26, 42 of the device 10 or 24 can be used to put a score line 44 on the material 46, for example drywall, which allows the drywall to be easily "broken" at that score line. This is accomplished by engaging the downwardly depending tab or hook 48 of the tape measure on an edge of the work surface, measuring the desired distance, and using both hands to move the extended tape 30 along the edge of the work surface 46, while pressing the tape measure 12 towards the material 46 as it is moved downwardly or upwardly to create a scribe or scoring line 44 at which the drywall material will be broken.

As can be seen from the above description, the device 10 and 34 of the present invention enables carpenters, construction workers, etc. to mark measurements, scribe and score using both hands to operate the tape measure 12 without the need of awkwardly using a hand to obtain and mark the working surface with a pencil or other marking or scoring instrument. It is contemplated that the device 10 or 34 of the present invention will not only simplify the measurement marking process, but also ensure that more accurate measurement markings and score lines are created.

Although several embodiments have been described in detail for purposes of illustration, various modifications may be made without departing from the scope and spirit of the invention. Accordingly, the invention is not to be limited, except as by the appended claims.

What is claimed is:

1. A measurement marking and scoring device, comprising:
    a marking member formed integrally with a tape measure housing and extending beyond a front edge of the tape measure housing;
    a marking surface formed at a downwardly directed end of the marking member and defining a point or edge sufficiently sharp so as to cut into a working surface upon application of pressure to the marking member or tape measure housing;
    an alignment tab extending from the marking member so as to be positioned over indicia of a tape extended from the tape measure housing.

2. The device of claim 1, wherein the marking member comprises a generally inverted L-shaped metallic extension extending from the tape measure housing and defining the marking surface at a lower end thereof.

3. The device of claim 1, wherein the metal marking surface is sufficiently sharp so as to be capable of cutting a score line in a drywall working surface such that the drywall can be broken along the cut score line.

4. The device of claim 1, wherein the marking surface and marking member are formed integrally with the device.

5. The device of claim 1, wherein the marking surface comprises a dual-beveled edge.

6. A measurement marking and scoring device, comprising:
    a platform configured to be affixed to a base of a tape measure housing;
    a marking member extending from the platform so as to be positioned beyond a front edge of the attached tape measure housing; and
    a metal marking surface integrally formed with the marking member at a downwardly directed end of the marking member and defining a point or edge sufficiently sharp so as to cut into a working surface upon application of pressure to the marking member or tape measure housing;
    wherein the marking member comprises a neck extending from the platform to an inverted U-shaped head positioned beyond the front edge of the tape measure housing and defining the marking surface at a lower end thereof.

7. The device of claim 6, wherein the metal marking surface is sufficiently sharp so as to be capable of cutting a score line in a drywall working surface such that the drywall can be broken along the cut score line.

8. The device of claim 6, wherein the marking surface and marking member are formed integrally with the device.

9. The device of claim 6, wherein the marking surface comprises a dual-beveled edge.

10. A measurement marking and scoring device, comprising:
    a platform configured to be affixed to a base of a tape measure housing;
    a marking member extending from the platform so as to be positioned beyond a front edge of the attached tape measure housing;
    a metal marking surface integrally formed with the marking member at a downwardly directed end of the marking member and defining a point or edge sufficiently sharp so as to cut into a working surface upon application of pressure to the marking member or tape measure housing; and
    an alignment tab extending from the marking member so as to be positioned over indicia of a tape extended from the tape measure housing.

11. The device of claim 10, wherein the marking member comprises a neck extending from the platform to an inverted U-shaped head positioned beyond the front edge of the tape measure housing and defining the marking surface at a lower end thereof.

12. The device of claim 10, wherein the metal marking surface is sufficiently sharp so as to be capable of cutting a score line in a drywall working surface such that the drywall can be broken along the cut score line.

13. The device of claim 10, wherein the marking surface and marking member are formed integrally with the device.

14. The device of claim 10, wherein the marking surface comprises a dual-beveled edge.

* * * * *